US008440464B2

(12) United States Patent
Fujii

(10) Patent No.: US 8,440,464 B2
(45) Date of Patent: May 14, 2013

(54) METHOD FOR EVALUATION OR SELECTION OF ADIPONECTIN SECRETION REGULATOR

(75) Inventor: Akihiko Fujii, Haga-gun (JP)

(73) Assignee: Kao Corporation, Tokyo (JP)

( * ) Notice: Subject to any disclaimer, the term of this patent is extended or adjusted under 35 U.S.C. 154(b) by 307 days.

(21) Appl. No.: 12/988,108

(22) PCT Filed: Apr. 14, 2009

(86) PCT No.: PCT/JP2009/001720
§ 371 (c)(1),
(2), (4) Date: Oct. 15, 2010

(87) PCT Pub. No.: WO2009/128257
PCT Pub. Date: Oct. 22, 2009

(65) Prior Publication Data
US 2011/0033877 A1 Feb. 10, 2011

(30) Foreign Application Priority Data

Apr. 16, 2008 (JP) .................. 2008-107047

(51) Int. Cl.
G01N 33/74 (2006.01)
G01N 33/68 (2006.01)
A61B 5/00 (2006.01)

(52) U.S. Cl.
USPC .............................. 436/86; 436/87; 600/300

(58) Field of Classification Search ........................ None
See application file for complete search history.

(56) References Cited

U.S. PATENT DOCUMENTS

| 2007/0065891 A1 | 3/2007 | Ebinuma et al. |
| 2007/0203061 A1 | 8/2007 | Kadowaki et al. |
| 2008/0139468 A1 | 6/2008 | Maeda et al. |

FOREIGN PATENT DOCUMENTS

| CN | 1864067 A | 11/2006 |
| CN | 1969187 A | 5/2007 |
| EP | 1 757 302 A1 | 2/2007 |
| JP | 2005-232059 A | 9/2005 |
| JP | A-2006-273839 | 10/2006 |
| JP | A-2007-075071 | 3/2007 |
| KR | 10-2006-0115977 A | 11/2006 |
| WO | WO 2005/094866 A1 | 10/2005 |
| WO | WO 2009/019208 | 2/2009 |

OTHER PUBLICATIONS

Neto et al. "Sleep deprivation affects inflammatory marker expression in adipose tissue" Lipids Health Dis. 2010; 9: 125, pp. 1-6.*
Taheri et al. "Short Sleep Duration Is Associated with Reduced Leptin, Elevated Ghrelin, and Increased Body Mass Index" PLoS Med. Dec. 2004;1(3):e62, pp. 210-217.*
Magee et al. "Acute sleep restriction alters neuroendocrine hormones and appetite in healthy male adults" Sleep and Biological Rhythms 2009; 7: 125-127.*
Simpson et al. "Effects of sleep restriction on adiponectin levels in healthy men and women" Physiol Behav. Dec. 2, 2010; 101(5): 693-698.*
Extended European Search Report for EP Appl. No. 09732309.1, including the Supplementary European Search Report and the European Search Opinion, mailed Jan. 4, 2012, from the European Patent Office, Munich, Germany.
de Mattos, ABM et al., "Dietary fish oil did not prevent sleep deprived rats from a reduction in adipose tissue adiponectin gene expression," Lipids Health Dis 7: 43 (doi:10.1186/1476-511X-7-43), 11 pages, (Nov. 2008), BioMed Central Open Access, England.
Kotani, K. et al., "Serum adiponectin levels and lifestyle factors in Japanese men," Heart and Vessels 22(5): 291-296 (Sep. 2007), Springer-Verlag, Tokyo, Japan.
Nakagawa, Y. et al., "Nocturnal reduction in circulating adiponectin concentrations related to hypoxic stress in severe obstructive sleep apnea-hypopnea syndrome," Am J Physiol Endocrinol Metab 294: E778-E784 (Apr. 2008; first published Jan. 15, 2008 doi:10.1152/ajpendo.00709.2007), American Physiological Society, Bethesda, MD.
Database World Patent Index Accession No. 2007-384058, English Language abstract for KR 2006 0115977, Nov. 13, 2006, Green Cross Corp.
Translation of International Search Report for PCT/JP2009/001720; I.A. fd: Apr. 14, 2009, mailed May 26, 2009 from the Japanese Patent Office, Tokyo, Japan.
International Preliminary Report on Patentability, Chapter I of the Patent Cooperation Treaty, including a translation of the Written Opinion for PCT/JP2009/001720; I.A. fd: Apr. 14, 2009, issued Nov. 30, 2010 from the International Bureau of WIPO, Geneva, Switzerland.
Araki, K. et al., "Telmisartan Prevents Obesity and Increases the Expression of Uncoupling Protein 1 in Diet-Induced Obese Mice," Hypertension 48:51-57 (Jul. 2006), American Heart Assoc., Dallas, TX.
Arita, Y. et al., "Paradoxical decrease of an adipose-specific protein, adiponectin, in obesity," Biochem Biophys Res Commun 257(1): 79-83 (Apr. 1999), Academic Press, United States.
Fasshauer, M. et al., "Hormonal regulation of adiponectin gene expression in 3T3-L1 adipocytes," Biochem Biophys Res Commun 290(3): 1084-1089 (Jan. 2002), Academic Press, United States.
Fujita, H. et al., "Effects of antidiabetic treatment with metformin and insulin on serum and adipose tissue adiponectin levels in db/db mice," Endocr J 52(4): 427-433 (Aug. 2005), Japan Endocrine Society, Japan.
Galisteo, M. et al., A Diet Supplemented with Husks of *Plantago ovata* Reduces the Development of Endothelial Dysfunction, Hypertension, and Obesity by Affecting Adiponectin and TNF-α in Obese Zucker Rats J Nutr 135: 2399-2404 (Oct. 2005), American Society of Nutritional Sciences, United States.

(Continued)

*Primary Examiner* — Christine Foster
(74) *Attorney, Agent, or Firm* — Sterne, Kessler, Goldstein & Fox P.L.L.C.

(57) ABSTRACT

Provided is a method for conveniently and rapidly evaluating or selecting an adiponectin secretion regulator.
The method for evaluating or selecting an adiponectin secretion regulator includes the following steps (A) to (C): (A) a step of administering a test substance to an experimental animal; (B) a step of inducing a sleep deprivation in the experimental animal; and (C) a step of measuring blood adiponectin level of the animal, and evaluating change of the blood adiponectin level.

4 Claims, 2 Drawing Sheets

OTHER PUBLICATIONS

CM Halleux, CM et al., "Secretion of adiponectin and regulation of apM1 gene expression in human visceral adipose tissue," Biochem Biophys Res Commun 288(5): 1102-1107 (Nov. 2001), Academic Press, United States.

Haluzik, M. et al., "Genetic Background (C57BL/6J Versus FVB/N) Strongly Influences the Severity of Diabetes and Insulin Resistance in ob/ob Mice," Endocrinology 145: 3258-3264 (Jul. 2004), Endocrine Society, United States.

Kadowaki, T et al., "Adiponectin and adiponectin receptors in insulin resistance, diabetes, and the metabolic syndrome," J Clin Invest 116(7): 1784-1792 (Jul. 2006), American Society for Clinical Investigation, United States.

Spranger, J. et al., "Adiponectin and protection against type 2 diabetes mellitus," Lancet 361(9353): 226-228 (Jan. 2003), Lancet Publishing Group, United States.

Stefan, N. et al., "Plasma adiponectin concentration is associated with skeletal muscle insulin receptor tyrosine phosphorylation, and low plasma concentration precedes a decrease in whole-body insulin sensitivity in humans," Diabetes 50:1884-1888 (Jun. 2002), American Diabetes Association, United States.

Tasali, E. et al., Slow-wave sleep and the risk of type 2 diabetes in humans Proc. Nat'l Acad Sci USA 105: 1044-1049 (Jan. 2008), National Academy of Sciences, United States.

Tsuchida, A. et al. "Peroxisome proliferator—activated receptor (PRAR)$\alpha$ activation increases adiponectin receptors and reduces obesity-related inflammation in adipose tissue," Diabetes 54:3358-3370 (Dec. 2005), American Diabetes Association, United States.

"Notification of First Office Action," for Chinese patent application No. 200980113310.1, mailed Jan. 30, 2013, Patent Office of the People's Republic of China, Beijing, China.

\* cited by examiner

METHOD FOR EVALUATION OR SELECTION OF ADIPONECTIN SECRETION REGULATOR

FIELD OF THE INVENTION

The present invention relates to a method for evaluating or selecting an adiponectin secretion regulator.

BACKGROUND OF THE INVENTION

In recent years, adiponectin, which is a factor (adipokine) generally secreted from adipocytes, has been reported to have an insulin-resistance-ameliorating effect or an anti-arteriosclerotic effect (Non-Patent Document 1). Hitherto, adipokines other than adiponectin (e.g., TNF-α, resistin, and free fatty acids) are known to induce insulin resistance. Unlike the cases of many adipokines, adiponectin ameliorates insulin resistance; i.e., adiponectin is a "good" adipokine, and thus it has recently become of great interest.

Some clinical data have shown that adiponectin has the aforementioned effects and, in addition, a reduction in blood adiponectin level can be used as a marker for predicting the onset of diabetes (Non-Patent Document 2). Blood adiponectin level has been reported to be inversely correlated with the degree of obesity (Non-Patent Document 3), and adiponectin reduction has been considered to play an important role in development or exacerbation of obesity-induced insulin resistance, diabetes or cardiovascular diseases. Therefore, a substance which promotes secretion of adiponectin has been considered to be useful for preventing or ameliorating such a disease.

There have been established several in vitro test systems for measuring adiponectin expression level. For example, as has been reported, in a system in which 3T3-L1 cells (i.e., preadipocyte cell line) have been differentiated, adiponectin expression level is reduced through addition of, for example, TNF-α (tumor necrosis factor α), insulin, or dexamethason (Non-Patent Document 4).

Also, adiponectin expression level has been measured in a test system employing adipocytes isolated upon abdominal surgery (Non-Patent Document 5). As has been reported, in vitro screening of adiponectin expression inducers can be carried out by use of cells harboring an enhancer element of adiponectin and reporter gene (Patent Document 1).

In an in vivo test system, an obese diabetic animal model (e.g., KKAy mouse (Non-Patent Document 6), db/db mouse (Non-Patent Document 7), ob/ob mouse (Non-Patent Document 8), C57BL/6 mouse (Non-Patent Document 9), or Zucker fatty (Non-Patent Document 10)) has been used for evaluating, for example, adiponectin secretion ability, since such an obese diabetic animal model develops obesity, insulin resistance, hypertriglyceridemia, or the like under high-fat diet, and the animal model shows a reduction in blood adiponectin level in association with obesity.

However, such a test system poses problems in that the test system requires a long period of time for evaluating change in amount of adiponectin secreted in an animal model, since the animal model must be reared under high-fat diet for at least several weeks until blood adiponectin level is reduced in the animal model.

PRIOR ART DOCUMENT

Patent Document

Patent Document 1: WO 2005/094866 pamphlet

Non-Patent Document

Non-Patent Document 1: Kadowaki, T., et al.: J. Clin. Invest., 116: 1784. 1792 (2006)
Non-Patent Document 2: Spranger, J., at al.: Lancet., 361: 226-228 (2003)
Non-Patent Document 3: Arita, Y., et al.: Biochem. Biophys. Res. Commun., 257: 79-83 (1999)
Non-Patent Document 4: Fasshauer., et al.: Biochem. Biophys. Res. Commun. 290: 1084-1089 (2002)
Non-Patent Document 5: Halleux, CM., et al.: Biochem. Biophys. Res. Commun. 288: 1102-1107 (2001)
Non-Patent Document 6: Tsuchida A., et al.: Diabetes.; 54 (12): 3358-3370 (2005)
Non-Patent Document 7: Fujita H., et al.: Endocrine J.; 52: 427-433 (2005)
Non-Patent Document 8: Haluzik M., et al.: Endocrinology.; 145: 3258-3264, (2004)
Non-Patent Document 9: Araki K., et al.: Hypertension.; 48: 51-57, (2006)
Non-Patent Document 10: Galisteo M., et al.: J. Nutr. 135: 2399-2404, (2005)

SUMMARY OF THE INVENTION

The present invention provides a method for evaluating or selecting an adiponectin secretion regulator, characterized by including the following steps (A) to (C):

(A) a step of administering a test substance to an experimental animal;
(B) a step of inducing a sleep deprivation in the experimental animal; and
(C) a step of measuring blood adiponectin level of the animal, and evaluating change of the blood adiponectin level.

DETAILED DESCRIPTION OF THE INVENTION

Figure 1:
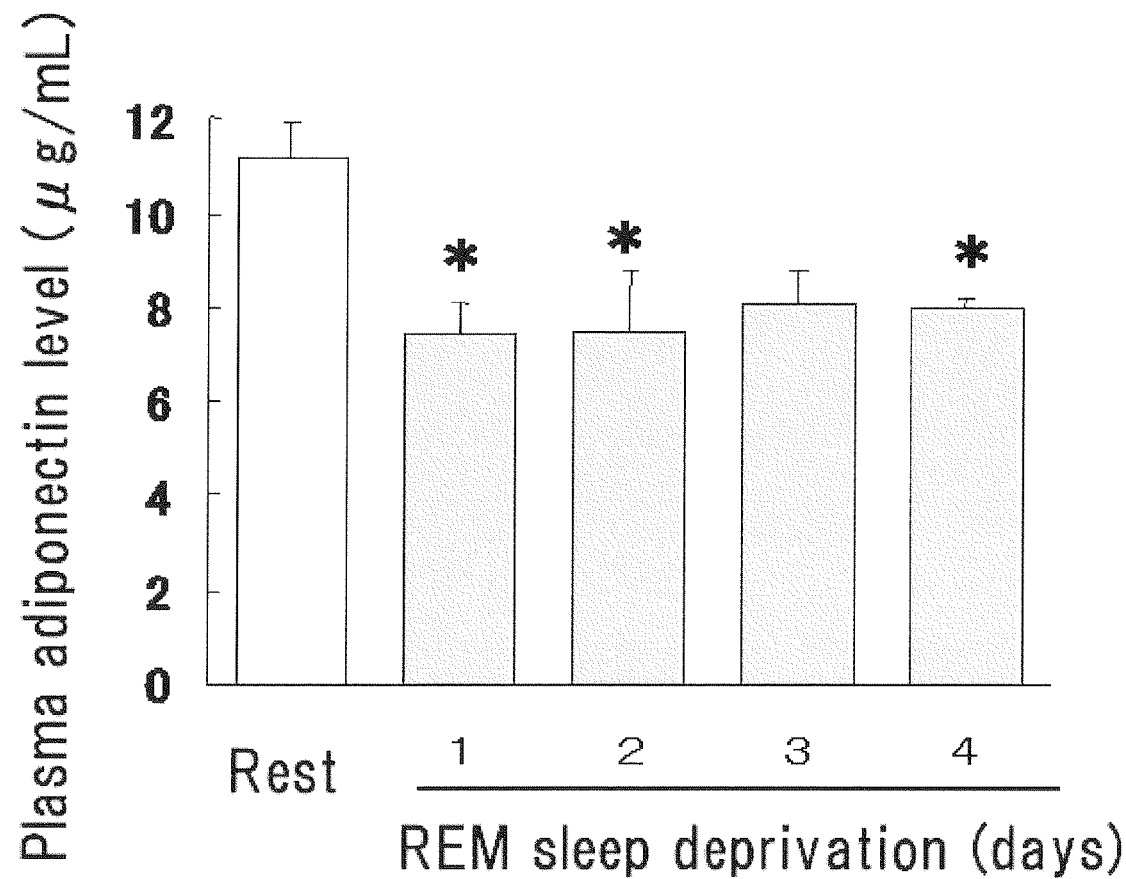
FIG. 1 is a graph showing a reduction in plasma adiponectin level caused by REM sleep deprivation. *$P<0.05$ (Dunnet Test, vs. Rest Group).

The present invention is directed to provision of a method for conveniently and rapidly evaluating or selecting an adiponectin secretion regulator in vivo.

The present inventor has conducted studies on screening systems employing animals, and has found that, unexpectedly, the blood adiponectin level of a sleep deprivation model is reduced within a short period of time after induction of a sleep deprivation, and an adiponectin secretion regulator can be evaluated or selected by use of such a sleep deprivation model.

According to the present invention, an adiponectin secretion regulator can be conveniently and rapidly evaluated or selected. Therefore, the present invention is useful as a screening method for conveniently selecting an agent for preventing or ameliorating a dysmetabolic syndrome (e.g., carbohydrate metabolism disorder or lipid metabolism disorder) or a disease caused by such a syndrome.

As shown in the Example described hereinbelow, in a sleep-deprivation-induced animal model, blood adiponectin level was reduced within a short period of time after induction of a sleep deprivation. A reduction in blood adiponectin level was suppressed through administration of chlorogenic acid, which has been reported to have the effect of promoting adiponectin secretion (JP-A-2005-232059), or an insulin-sensitizing effect and cholesterol- and triglyceride-lowering effect in vivo (Journal of Nutritional Biochemistry 13 (2002), 717-726). Thus, a sleep deprivation model system can be employed for evaluation or selection of an adiponectin secretion regulator which promotes or suppresses adiponectin secretion.

The method for evaluating or selecting an adiponectin secretion regulator of the present invention is described in below.

The experimental animal employed in the present invention is not particularly limited, so long as it can be an experimental small animal which can be used as a sleep deprivation model. The experimental animal is preferably, for example, a rodent such as a mouse, rat, or guinea pig.

As used herein, a "sleep deprivation" induced in an animal refers to, for example, a sleep deprivation which is induced by any of known sleep deprivation methods devised for the purpose of studying the meaning of sleep in organisms. In the present invention, the "sleep deprivation" induced in an animal is preferably REM sleep deprivation.

Examples of known sleep deprivation methods include the below-described methods. Particularly, the platform method is preferably employed.

1) The platform method (Youngblood B D., et al., Physiol. Behay. 67 (5) 643-649, (1999)). The platform method, which is also called "flower pot method," is a typical sleep deprivation method.

This method can particularly induce REM sleep deprivation in a relatively specific manner.

In this method, water is added to a cage, and a small cylindrical platform on which an experimental animal can ride is placed in the cage. Although an animal can take a rest on the platform, when falling into REM sleep, the animal comes into contact with water, due to loss of balance in association with muscle relaxation; i.e., the animal can have non-REM sleep, but cannot have REM sleep.

Specifically, a stainless steel cylinder (diameter: 6 to 7 cm) is placed in a rat breeding cage made of acrylic resin, and water is added to the cage so that the water level is adjusted to 1 to 2 cm below the top of the cylinder. One rat (250 to 400 g) is reared in the cage under the conditions that the rat can take feed and drinking water ad libitum.

2) The treadmill (or disk) method (Guzman-Marin R., et al. Eur. J. Neurosci. 22 (8): 2111-2116 (2005), Everson Calif., et al. Am. J. Physiol. Endocrinol. Metab. 286: 1060-1070 (2004)).

In this method, a treadmill or a rotatable disk is placed in a cage, and the treadmill or the disk is periodically operated for sleep deprivation of an animal in the cage.

3) A sleep deprivation method by means of noise during rearing (Rabat A., et al. Brain Res. 1059: 82-92 (2005)).

In this method, a noise (frequency: 20 to 300 Hz, intensity: 70 to 80 db) is irregularly output from a speaker for sleep deprivation of an animal.

4) A method in which an animal is deprived of sleep by means of handling thereof (Toru M., et al. Pharmacol. Biochem. Behay. 20 (5): 757-761 (1984)).

In this method, when an animal falls asleep, the animal is touched with a hand for sleep deprivation.

The period of the sleep deprivation, which may vary with the sleep derivation method employed, is generally about one day to about five days. When the platform method is employed, the period of the sleep deprivation may be about one day to about two days, since blood adiponectin level is significantly reduced one day after induction of a sleep deprivation.

The timing of administration of a test substance may be appropriately determined in consideration of the intended use of the substance. Administration of a test substance may be carried out before or after induction of a sleep deprivation in an experimental animal, or may be carried out during a sleep deprivation.

Administration of a test substance may be carried out through any of, for example, oral, transdermal, subcutaneous, intradermal, intramuscular, tail vein, and intraperitoneal routes. Oral administration is preferable.

Serum or plasma adiponectin level may be determined through, for example, ELISA (enzyme-linked immunosorbent assay), radioimmunoassay, or western blotting.

Specifically, serum or plasma adiponectin level may be determined by means of, for example, a rat adiponectin ELISA kit (product of AdipoGen).

Thus, a test substance (i.e., an adiponectin secretion regulator) can be evaluated or selected on the basis of the blood adiponectin level of a subject to which the substance has been administered. In this case, when, for example, the blood adiponectin level of the subject is statistically significantly higher than that of a control subject to which the test substance has not been administered, the test substance can be evaluated or selected as an adiponectin secretion promoter.

Examples of the adiponectin secretion promoter include substances which ameliorate low adiponectin state through, for example, enhancement of expression of adiponectin. Such an adiponectin secretion promoter may be provided in the form of a drug or food for prevention, treatment, or amelioration of diseases or symptoms caused by low adiponectin state, including hypoadiponectinemia, impaired glucose tolerance, diabetes, type 2 diabetes mellitus, insulin resistance syndrome, diabetic complication, hyperglycemia, arteriosclerosis, atherosclerosis, cardiovascular disease, cerebrovascular disorder, vascular stenosis, peripheral vascular disease, aneurysm, hyperlipidemia, hypercholesterolemia, and obesity.

EXAMPLE

1. Method

SD rats (male, 10 to 11 weeks old) were divided into groups, each containing rats with similar body weights. A cylindrical platform (diameter: 6.0 cm, height: 2.5 cm) on which a rat can take a rest was placed in a cage, and water was added to the cage so that the water level was adjusted to 1 cm below the top of the platform. Each rat was reared for one to four days in the cage (one rat/cage). Rats of a rest group were reared in cages each containing a common floorcloth (N=4 for each group). In a chlorogenic acid administration experiment, rats were reared in cages for 30-hour REM sleep deprivation. Rats of a chlorogenic acid (5-CQA, product of Sigma) administration group orally received chlorogenic acid thrice every 12 hours by means of a probe (dose: 150 mg/kg (300 mg/kg/day)). Rats of a control group received distilled water. Rats of a rest group were reared in cages each containing a common floorcloth, and received distilled water (N=6 for each group). Immediately after REM sleep deprivation, under anesthesia with FORANE® (isoflurane; product of Dainippon Pharmaceutical Co., Ltd.), blood was collected from each rat through the abdominal aorta into a VENOJECT® vacuum blood collection tube. Plasma collected in a heparin containing tube was stored at −80° C. until use. The plasma adiponectin level was determined by means of a rat adiponectin ELISA kit (product of ADIPOGEN®). Specifically, plasma was 1,000-fold diluted with a dilution buffer contained in the kit, and then plasma adiponectin level was determined according to the kit protocol.

2. Results (1) Effect of REM Sleep Deprivation on Plasma Adiponectin Level

In rats of the sleep deprivation group, plasma adiponectin level was significantly reduced only one day after REM sleep deprivation (also, two days and four days after REM sleep deprivation), as compared with the case of rats of the rest group. However, a reduction in plasma adiponectin level did not depend on the period of REM sleep deprivation; i.e., the degree of reduction in plasma adiponectin level was almost the same from one day to four days after REM sleep deprivation (FIG. 1).

Figure 2:
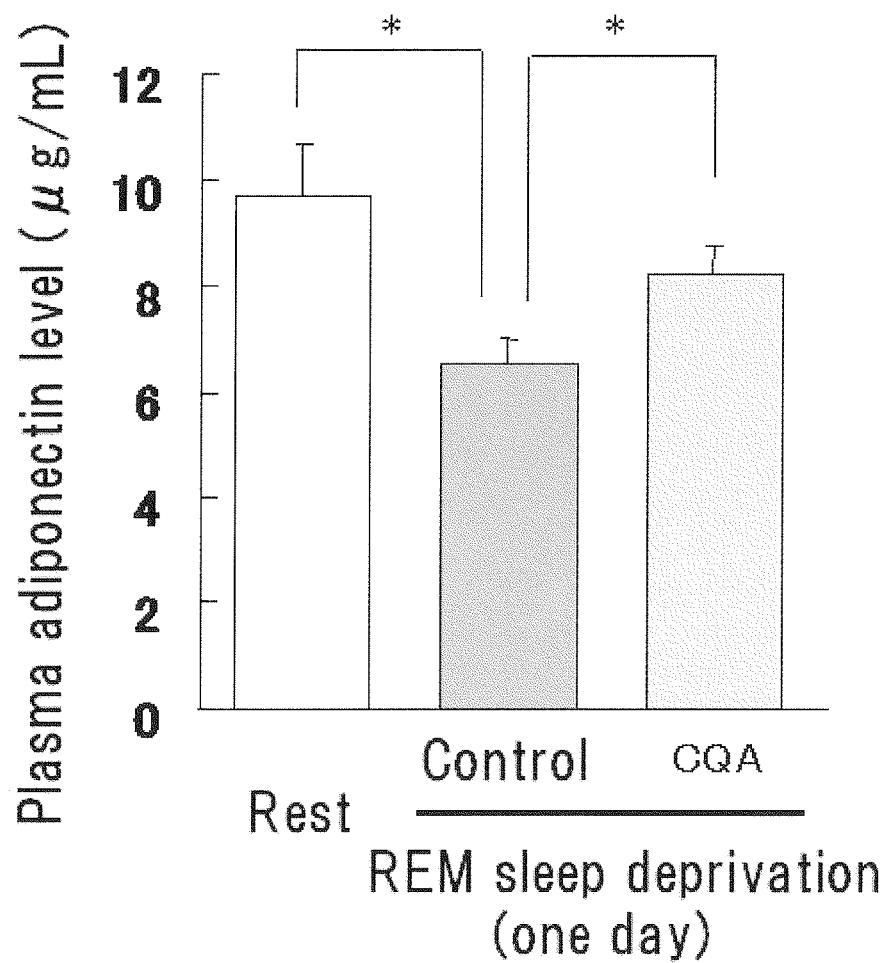
FIG. 2 is a graph showing the effect of chlorogenic acid on a reduction in plasma adiponectin level caused by REM sleep deprivation. *$P<0.05$ (Fisher's PLSD test).

(2) Effect of Chlorogenic Acid on Reduction in Plasma Adiponectin Level Caused by REM Sleep Deprivation REM sleep deprivation significantly reduced plasma adiponectin level, and chlorogenic acid (CQA) significantly suppressed a reduction in plasma adiponectin level caused by REM sleep deprivation (FIG. 2).

Thus, in a REM sleep deprivation system, blood adiponectin level is reduced within a very short period of time. Therefore, such a system can be employed for effective screening of adiponectin secretion regulators.

The invention claimed is:

1. A method for evaluating or selecting a test substance that regulates an animal's blood adiponectin level, comprising the following steps (A) to (E):
   (A) a step of administering a test substance to an experimental animal that is a rat;
   (B) a step of inducing sleep deprivation in the experimental animal;
   (C) a step of measuring the animal's blood adiponectin level after sleep deprivation;
   (D) a step of comparing the animal's blood adiponectin level after sleep deprivation to a blood adiponectin level in a control animal after sleep deprivation, wherein the control animal did not receive the test substance; and
   (E) a step of evaluating or selecting a test substance that changes the experimental animal's blood adiponectin level relative to that of the control animal in step (D) as a substance that regulates blood adiponectin level.

2. The method according to claim 1, wherein the sleep deprivation is rapid eye movement sleep deprivation.

3. The method according to claim 2, wherein a platform method is used to induce the rapid eye movement sleep deprivation.

4. The method according to any one of claim 1 to 3, wherein when the test substance suppresses a sleep deprivation-induced reduction in the experimental animal's blood adiponectin level, as compared with a sleep deprivation-induced reduction in the control animal's blood adiponectin level, the test substance is evaluated or selected in step (E) as a substance that regulates blood adiponectin level.

* * * * *